(12) United States Patent
Scotto et al.

(10) Patent No.: US 11,666,883 B2
(45) Date of Patent: Jun. 6, 2023

(54) PLANT FOR THE SYNTHESIS OF MELAMINE WITH OFFGAS RECOVERY IN A TIED-IN UREA PLANT

(71) Applicant: Casale SA, Lugano (CH)

(72) Inventors: Andrea Scotto, Breganzona (CH); Matteo Fumagalli, San Fermo della Battaglia (IT)

(73) Assignee: Casale SA, Lugano (CH)

( * ) Notice: Subject to any disclaimer, the term of this patent is extended or adjusted under 35 U.S.C. 154(b) by 0 days.

(21) Appl. No.: 16/964,839

(22) PCT Filed: Jan. 14, 2019

(86) PCT No.: PCT/EP2019/050746
§ 371 (c)(1),
(2) Date: Jul. 24, 2020

(87) PCT Pub. No.: WO2019/145169
PCT Pub. Date: Aug. 1, 2019

(65) Prior Publication Data
US 2021/0060519 A1 Mar. 4, 2021

(30) Foreign Application Priority Data
Jan. 26, 2018 (EP) .................................. 18153653

(51) Int. Cl.
*B01J 19/24* (2006.01)
*B01J 3/03* (2006.01)
*C07C 273/04* (2006.01)
*C07D 251/60* (2006.01)

(52) U.S. Cl.
CPC ............... *B01J 19/245* (2013.01); *B01J 3/03* (2013.01); *C07C 273/04* (2013.01); *C07D 251/60* (2013.01); *B01J 2219/0004* (2013.01); *B01J 2219/00024* (2013.01)

(58) Field of Classification Search
CPC ....... B01J 3/00; B01J 3/03; B01J 19/00; B01J 19/24; B01J 19/245; B01J 2219/00;
(Continued)

(56) References Cited

U.S. PATENT DOCUMENTS 6,114,579 A 9/2000 Van Wijck
6,790,956 B1 * 9/2004 Coufal ................. C07D 251/60
544/203

(Continued)

FOREIGN PATENT DOCUMENTS

EP 1752447 A1 2/2007
EP 1918274 A1 5/2008
EP 2940006 A1 11/2015

OTHER PUBLICATIONS

International Preliminary Report on Patentability issued in connection with PCT/EP2019/050746.
(Continued)

*Primary Examiner* — Natasha E Young
(74) *Attorney, Agent, or Firm* — Akerman LLP

(57) ABSTRACT

Plant for the synthesis of melamine starting from urea, wherein the stream of offgas containing NH3 and CO2 produced by the synthesis of melamine is converted into urea in a dedicated urea plant.

15 Claims, 1 Drawing Sheet

(58) Field of Classification Search
CPC .... B01J 2219/00002; B01J 2219/00018; B01J 2219/0002; B01J 2219/00024; B01J 2219/00027; B01J 2219/0004; C07C 273/00; C07C 273/02; C07C 273/04; C07D 251/00; C07D 251/02; C07D 251/12; C07D 251/26; C07D 251/40; C07D 251/54; C07D 251/56; C07D 251/60

See application file for complete search history.

(56) References Cited

U.S. PATENT DOCUMENTS

| | | | | |
|---|---|---|---|---|
| 7,414,130 B2* | 8/2008 | Brunengo | ............ | C07C 273/12 |
| | | | | 544/201 |
| 2003/0028020 A1* | 2/2003 | Gupta | ................ | C07D 251/62 |
| | | | | 544/203 |

OTHER PUBLICATIONS

International Search Report issued in connection with PCT/EP2019/050746.
Guan Lu-Feng, "Process of Co-Production and Technological Modification of Melamine and Urea," Modern Chemical History, 2006, pp. 45-48.
Zardi, F., "Integration of Urea and Melamine Plants—Casale Experience," GazChem, 2007.
"Urea-Melamine Plant Integration," Nitrogen + Syngas, vol. 321, pp. 44-54, Jan.-Feb. 2013.

* cited by examiner

PLANT FOR THE SYNTHESIS OF MELAMINE WITH OFFGAS RECOVERY IN A TIED-IN UREA PLANT

CROSS-REFERENCE TO RELATED APPLICATIONS

This application is a national phase of PCT/EP2019/050746, now WO 2019/145169, filed Jan. 14, 2019, and claims priority to EP 18153653.3, filed Jan. 26, 2018, the entire contents of both of which are hereby incorporated by reference.

FIELD OF APPLICATION

The invention relates to the field of combined production of melamine and urea.

PRIOR ART

Melamine is industrially produced starting from urea by the following reaction:

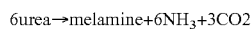

wherein ammonia and carbon dioxide are in gaseous form and are termed offgas.

Two fundamental variants of the melamine synthesis process are known, which are termed low-pressure catalytic synthesis and high-pressure non-catalytic synthesis respectively. Both of them are based on the aforementioned reaction, which in the first case is carried out at a pressure of about 2-10 bar and in the second case is carried out at a pressure of 70 bar or more.

It is also known to combine a melamine plant with a tied-in urea plant where the melamine offgas are recycled to the production of urea. This combination is attractive because urea is industrially synthesized from ammonia and carbon dioxide.

In the prior art the combined production of urea and melamine operates essentially in the following manner: a urea synthesis plant produces urea from ammonia and carbon dioxide; at least a part of the urea produced supplies a melamine plant; the offgas extracted from the melamine plant are recycled to the urea plant.

This combination of the urea process and melamine process is applicable generally and independently of the type of the urea process, for example with urea being produced according to the CO2 stripping process, the ammonia stripping process or another, and of the low-pressure or high-pressure melamine process.

Different solutions are also known for recycling the offgas in the urea process, according to the urea process and the melamine process involved. In particular, in the case of a low-pressure melamine process, the offgas are generally recycled to the urea reactor in the form of an aqueous solution (after condensation), which however has the drawback of introducing water into the urea reactor. In the case of a high-pressure melamine process, instead, the offgas are available at high pressure, so as they may be recycled in anhydrous form, for example, by direct introduction into the condenser of the high-pressure urea synthesis loop.

Combined processes for the production of urea and melamine are described for example in EP 1 918 274 and EP 2 940 006.

The combination of said two processes is on the one hand advantageous, but poses a number of problems.

A first problem is that the urea synthesis process is subject to disturbances caused by the melamine process. For example a stoppage of the melamine plant may cause a stoppage of the urea plant. This problem is mainly felt in urea/melamine plants where the urea plant has a capacity (amount of urea produced) which is greater than the amount of urea required by the melamine plant. In these plants, only a part of the urea feeds the synthesis of melamine, the remaining part being sent to a different use or exported. Any stoppage of the melamine plant consequently affects not only the production of melamine, but also the production of urea to be exported, with consequent economic loss.

Another problem is that the combined melamine/urea plants are often the result of a revamping where a melamine plant is added to an already existing urea plant. The connection of the new melamine plant to the urea plant for offgas recovery generally requires a shutdown of the urea plant, for example in order to arrange a line for the introduction of the aqueous solution (containing the condensed melamine offgas) into the reactor, or a line for the introduction of the melamine offgas into the condenser, according to the aforementioned techniques. Clearly, the shutdown of the urea plant and the production downtime represent a considerable economic loss.

The efficiency of the existing urea plant is sometimes penalized, especially when the offgas are recycled in the form of an aqueous solution. It is well known that the presence of water in the reactor adversely affects the urea conversion yield.

Moreover the existing urea plant may be unable to convert the increased quantity of reagents due to the recovery from the new melamine plant. In this case a capacity increase of the urea plant may be costly.

EP 1 752 447 discloses a process for integrated production of urea and melamine wherein urea is synthesized in a first urea reactor; melamine offgas are sent to a second urea reactor which also receives the ammonium carbamate aqueous solution from a low-pressure recovery section; the effluent of the second urea reactor, together with the effluent of the first urea reactor, is sent to the recovery section.

SUMMARY OF THE INVENTION

The object of the present invention is to overcome the aforementioned drawbacks of the prior art.

This object is achieved with a combined melamine-urea plant according to claim 1.

The plant of the invention comprises a melamine plant for the synthesis of melamine from urea and a tied-in urea plant which is specifically dedicated to the synthesis of urea starting from the melamine offgas. The tied-in urea plant is therefore termed offgas-fed urea plant.

Said offgas-fed urea plant comprises a high-pressure (HP) urea synthesis section running at a synthesis pressure and at least one recovery section running at a recovery pressure lower than said synthesis pressure. The offgas-fed urea plant may comprise more than one recovery section at different recovery pressures, e.g. a medium-pressure (MP) recovery section and a low-pressure (LP) recovery section, wherein a urea solution effluent of the HP synthesis section is processed in the MP recovery section and a partly purified urea solution effluent of the MP recovery section is further processed in the LP recovery section.

The HP urea synthesis section includes at least a urea synthesis reactor where urea is synthesized from ammonia and carbon dioxide at a urea synthesis pressure. The urea synthesis pressure is at least 80 bar, preferably in the range 100 to 200 bar. The HP urea synthesis section may also comprise a HP stripper (where unconverted ammonia and carbon dioxide are removed from the reactor effluent) and a HP condenser (where a gas phase withdrawn from the stripper is condensed for subsequent recycle in the reactor) forming a loop together with the reactor, according to known technique.

A recovery section denotes a section where a urea-containing solution is processed by removing unconverted ammonia and carbon dioxide which are usually in the form of ammonium carbamate. A recovery section typically comprises a carbamate decomposer where the ammonium carbamate is decomposed to ammonia and carbon dioxide, and a condenser where the gas withdrawn from the carbamate decomposer are condensed to form a solution which is then recycled to the HP synthesis section.

The one or more recovery section(s) of the offgas-fed urea plant produces a purified urea aqueous solution which contains at least 65% urea (in weight) and balance water, with only minor amounts of unconverted matter and/or impurities.

Optionally, the offgas-fed urea plant may comprise a concentration section wherein the solution is concentrated to a higher content of urea, for example 95% or more. After this further concentration, the urea can be used for the synthesis of melamine. Optionally, the offgas-fed urea plant may also comprise a finishing section for the production of a solid urea product, e.g. by granulation or prilling.

Advantageously all or part of the urea produced by said offgas-fed urea plant supplies said melamine plant, i.e. is used to produce melamine.

The offgas-fed urea plant receives ammonia and CO2 supply mainly or exclusively from the offgas withdrawn from the tied-in melamine plant. Said stream of offgas provides at least 90% (mass) of ammonia and CO2 global input of said offgas-fed urea plant. Preferably at least 95% (mass) of the ammonia and CO2 global input of the offgas-fed urea plant comes from the melamine offgas.

Said offgas-fed urea plant may nevertheless receive an additional amount of ammonia and/or CO2. It is preferred that the sole supply of ammonia and CO2 to said plant consists of the melamine offgas. However when the melamine offgas do not provide the full input of reagents to said offgas-fed urea plant, the balance may be represented by fresh reagents.

The urea produced by the offgas-fed urea plant may be in the form of: a purified aqueous urea solution containing at least 65% urea by weight; a high purity urea melt (molten urea); a solid urea product preferably in the form of prills or granules.

A purified aqueous solution, with at least 65% urea, is obtained after processing the effluent of a high-pressure synthesis section in at least one recovery section for recovery of unconverted ammonia and carbon dioxide, according to known technique in the field of urea synthesis. Said offgas-fed urea plant includes the necessary items to produce this solution, for example a high-pressure synthesis equipment (e.g. a synthesis loop) followed by one or more recovery section(s) at a lower pressure.

Said offgas-fed urea plant may include, in some embodiments, a concentration section suitable to remove water from the urea solution. A concentration section may also be provided in the melamine plant.

To produce a molten urea stream, which may be directly suitable to make melamine, the offgas-fed urea plant may also include an evaporation section suitable to remove water from a urea solution and obtain molten urea. The molten urea preferably comprises at least 95% urea in weight. In the event that the offgas-fed urea plant is to produce solid urea, said plant may include a finishing section e.g. including a prilling tower and/or a granulator.

In some embodiments of the invention, the urea-melamine plant comprises a first urea plant and a second urea plant. The first urea plant may be referred to as main urea plant, while the second urea plant is the offgas-fed urea plant. The urea input of the melamine plant can be produced in part by the main urea plant and in part by the offgas-fed urea plant. A remaining amount of urea produced by the main plant, if any, can be exported for another use.

The first urea plant (main urea plant) may comprise a finishing section for the production of urea, e.g. by granulation or prilling. The production of solid urea, if provided, is preferably carried out in the main urea plant.

In embodiments with a first urea plant (main urea plant) and second urea plant (offgas-fed urea plant), said second urea plant preferably does not receive any recycled carbamate solution from the main urea plant.

In other embodiments, the melamine plant is at least partly supplied with imported urea, i.e. with urea produced elsewhere and not by the melamine-urea plant. The urea produced by offgas-fed urea plant advantageously forms part of the supply of the melamine plant. The offgas-fed urea plant may be the only urea section of the plant, i.e. a main urea plant may not be present.

Both the main urea plant (if present) and the offgas-fed urea plant may be operated according to different urea synthesis processes known in the literature. The melamine plant may be of the low pressure or high pressure type. The melamine offgas may contain water or be substantially anhydrous, depending on the technology used for the synthesis of melamine.

The conversion of the melamine offgas into urea may comprise a step of offgas condensation into an aqueous solution, within a suitable condensation section.

The urea supplying the melamine plant may be in the form of a urea melt, solid urea, or an aqueous solution of urea. If the supply is formed by an aqueous solution of urea, said solution is concentrated in an evaporation section which may belong to the melamine plant or to the offgas-fed urea plant.

The invention may be applied to the revamping of urea plants or revamping of combined urea/melamine plants, according to the claims.

One object of the invention is a method for revamping a urea plant comprising:

adding a melamine synthesis plant to said urea plant, wherein at least part of the urea produced in the existing urea plant is intended to supply said melamine synthesis plant;

adding a offgas-fed urea plant for conversion into urea of a stream of offgas extracted from the melamine plant, wherein said offgas stream provides at least 90% of the ammonia and CO2 supply of said added urea plant.

Another object of the invention is a method for revamping a urea/melamine plant, wherein the already existing plant comprises a melamine plant and a first urea plant, and the method comprises:

adding a second urea plant specifically dedicated to the synthesis of urea from the ammonia and carbon dioxide contained in the offgas coming from the melamine plant, wherein a stream of offgas extracted from the melamine plant provides at least 90% of the ammonia and CO2 supply of said second urea plant.

In this case the existing first urea plant may be defined as the main urea plant. The method may comprise the operation of re-directing offgas originally directed to the main urea plant towards the newly installed second urea plant.

The added urea plant is suitable to produce a urea product which is any of: an aqueous urea solution comprising at least 65% urea in weight; a molten urea, a solid urea product. The added urea plant includes a high-pressure synthesis loop followed by one or more recovery sections. The added urea plant optionally includes a concentration section suitable to remove water and a finishing section suitable to produce a solid urea product.

The invention offers the following advantages:

it allows the use, as raw material, of urea (in solid form or as an aqueous solution) coming from the outside and not produced in loco, for example solid urea supplied through special transportation means;

no worsening in the performances of the urea synthesis plant due to the recovery of the offgas of the melamine plant;

in the event of construction of a new melamine plant supplied with urea coming from an existing plant, the latter does not require any type of revamping or action because the offgas are recovered in the specially provided plant;

the urea synthesis plant dedicated to the offgas recovery is constructed together with the melamine plant, consequently it is not required to interrupt the urea production of the main plant for the operations of integration with the new melamine plant;

the "main" urea plant is not disturbed by any downtime or malfunctioning of the melamine plant which may alter the quantity and/or composition of the offgas by-products;

urea coming from plants which are not in the vicinity of the melamine plant may be used as raw material.

The advantages of the invention will become even clearer with the aid of the following description, in which FIG. 1 and FIG. 2 illustrate in schematic form two embodiments of the invention.

DESCRIPTION OF PREFERRED EMBODIMENTS

Figure 1:
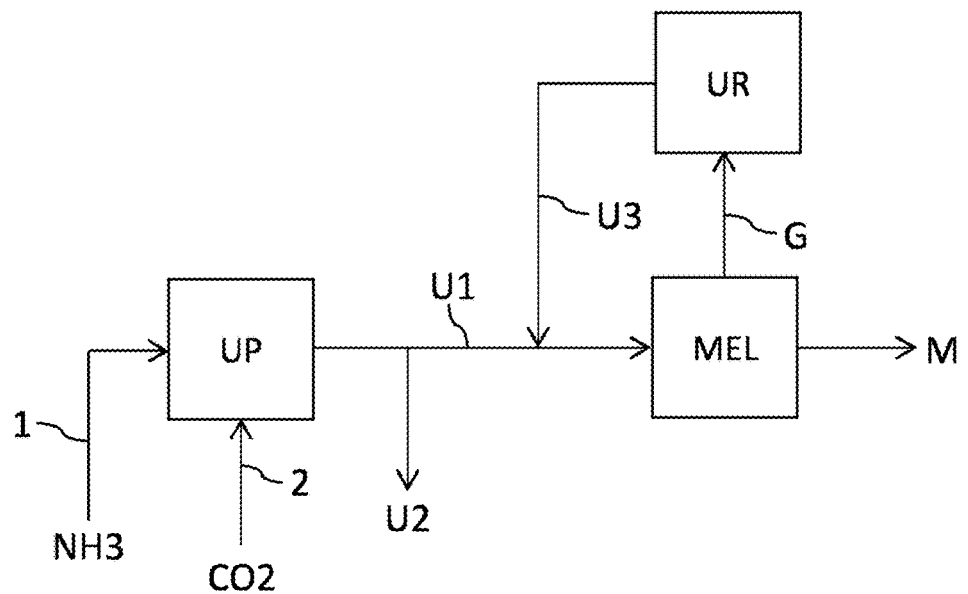
FIG. 1 is an illustration of a combined urea/melamine plant of a first embodiment of the invention.

FIG. 1 shows in schematic form a combined urea/melamine plant comprising:
a first urea plant UP (main urea plant),
a melamine plant MEL,
a second urea plant UR which is dedicated to the synthesis of urea from the offgas coming from said melamine plant MEL.

The main urea plant UP is supplied with a stream 1 of ammonia and with a stream 2 of CO2.

A part U1 of the urea produced by the main urea plant UP supplies the melamine plant MEL. Another part U2 is exported or sent to another use.

The urea U1 is preferably in the form of a urea melt or solid urea. The urea U2 may be in a similar form or in the form of an aqueous solution.

The melamine plant MEL produces melamine M and a stream G of offgas mainly containing NH3 and CO2.

Said stream G supplies the second urea plant UR which is dedicated to the recovery of the reagents contained in the offgas, by producing additional urea.

In the example, said stream G represents the sole supply of reagents, i.e. ammonia and CO2, of the second urea plant UR. Said urea plant UR does not have other inputs of ammonia and/or CO2. In some variants, if necessary, small additional inputs of ammonia and CO2 may be provided.

The use of melamine offgas to produce urea is also termed offgas recovery. The offgas stream G may be recovered in the urea plant UR for example by supplying the offgas in the form of an anhydrous gas or in an aqueous solution.

Recovery in an anhydrous form involves for example the introduction of the offgas into a high-pressure condenser of the urea plant UR, as described in EP 2 940 006.

Recovery in an aqueous solution involves for example a condensation step with water so as to form an aqueous solution containing ammonia and CO2 and the introduction of said solution in the urea reactor of the urea plant UR.

Said urea plant UR produces urea U3 which advantageously provides for the supply of the melamine plant MEL.

Figure 2:
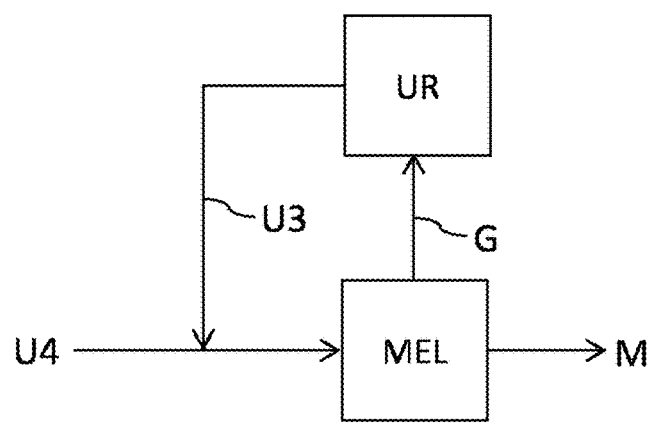
FIG. 2 is an illustration of a urea-melamine plant which does not comprise the urea synthesis plant UP of a second embodiment of the invention.

FIG. 2 shows an embodiment of a urea-melamine plant which does not comprise the main urea synthesis plant UP. The only urea synthesis plant in this embodiment is the offgas-fed urea plant UR.

In FIG. 2 the melamine plant MEL is supplied with urea U4 coming from an external source. The urea U3 produced in the urea plant UR is advantageously also returned to the melamine plant MEL.

What is claimed is:

1. A melamine-urea plant comprising:
a melamine plant (MEL) for the production of melamine starting from urea, obtaining a product stream containing melamine and a stream of offgas containing NH3 and CO2 in gaseous form;
a offgas-fed urea plant (UR) dedicated to the synthesis of urea starting from said stream of offgas, said offgas-fed urea plant being apt to produce urea starting from ammonia and CO2, and comprising at least a high-pressure synthesis section running at a synthesis pressure and a recovery section running at a recovery pressure lower than said synthesis pressure,
wherein said stream of offgas provides at least 90% of ammonia and CO2 supply of said offgas-fed urea plant.

2. The plant according to claim 1, wherein said stream of offgas provides the sole supply of ammonia and CO2 of said offgas-fed urea plant.

3. The plant according to claim 1, wherein all or part of the urea produced by said offgas-fed urea plant supplies said melamine plant.

4. The plant according to claim 1, wherein the offgas-fed urea plant further includes a concentration section arranged to receive a urea solution effluent from the recovery section and to produce a concentrated solution or a urea melt containing at least 95% urea.

5. The plant according to claim 4, wherein the offgas-fed urea plant further includes a finishing section to produce solid urea.

6. The plant according to claim 1, comprising:
a first urea plant, which is a main urea plant and comprises at least a high-pressure synthesis section running at a synthesis pressure and a recovery section running at a recovery pressure lower than said synthesis pressure,
a second urea plant, which is said offgas-fed urea plant, wherein a urea supply of said melamine plant is produced at least in part by said main urea plant.

7. The plant according to claim 6, wherein the urea supply of said melamine plant is produced in part by said main urea plant and in part by said second offgas-fed urea plant.

8. The plant according to claim 6, wherein a part of the urea produced by said second urea plant is exported from the plant.

9. The plant according to claim 1, wherein the urea product of said off-gas urea plant (UR) is any of: an aqueous urea solution comprising at least 65% urea in weight; a molten urea comprising at least 95% urea, a solid urea product.

10. The method for revamping a urea plant comprising:
adding a melamine synthesis section to said urea plant, wherein at least part of the urea produced in the existing urea plant is intended to supply said melamine synthesis section;
adding a second urea plant which is an offgas-fed urea plant for the production of urea starting from the melamine offgas withdrawn from said melamine plant, wherein a stream of offgas extracted from the melamine plant provides at least 90% of ammonia and CO2 supply of said second urea plant,
wherein said second urea plant comprises at least a high-pressure synthesis section running at a synthesis pressure and a recovery section running at a recovery pressure lower than said synthesis pressure.

11. The method according to claim 10, wherein the added urea plant is suitable to produce a urea product which is any of:
an aqueous urea solution comprising at least 65% urea in weight;
a molten urea comprising at least 95% urea, a solid urea product.

12. A method for revamping a urea/melamine plant, wherein the plant comprises a melamine plant and a tied-in urea plant, the method comprising:
adding a second urea plant specifically dedicated to the synthesis of urea from offgas coming from the melamine plant wherein a stream of offgas extracted from the melamine plant provides at least 90% of ammonia and CO2 supply of said second urea plant, and said second urea plant comprises at least a high-pressure synthesis section running at a synthesis pressure and a recovery section running at a recovery pressure lower than said synthesis pressure.

13. The method according to claim 12, wherein the second urea plant is suitable to produce a urea product which is any of:
an aqueous urea solution comprising at least 65% urea in weight;
a molten urea comprising at least 95% urea, a solid urea product.

14. The plant according to claim 1, wherein said synthesis pressure is at least 80 bar.

15. The plant according to claim 1, wherein said synthesis pressure is in the range of 100 to 200 bar.

* * * * *